United States Patent
Brommer

(10) Patent No.: US 12,059,003 B2
(45) Date of Patent: Aug. 13, 2024

(54) ANTIMICROBIAL COMPOSITIONS EFFECTIVE AGAINST BACTERIA AND FUNGUS

(71) Applicant: TerMir Inc., Raleigh, NC (US)

(72) Inventor: Chad L. Brommer, Raleigh, NC (US)

(73) Assignee: TerMir Inc., Raleigh, NC (US)

( * ) Notice: Subject to any disclaimer, the term of this patent is extended or adjusted under 35 U.S.C. 154(b) by 464 days.

(21) Appl. No.: 16/537,292

(22) Filed: Aug. 9, 2019

(65) Prior Publication Data

US 2019/0357536 A1 Nov. 28, 2019

Related U.S. Application Data

(63) Continuation of application No. PCT/US2018/041777, filed on Jul. 12, 2018.

(60) Provisional application No. 62/531,538, filed on Jul. 12, 2017, provisional application No. 62/531,528, filed on Jul. 12, 2017.

(51) Int. Cl.
*A01N 43/16* (2006.01)
*A01N 25/00* (2006.01)

(52) U.S. Cl.
CPC ............. *A01N 43/16* (2013.01); *A01N 25/00* (2013.01)

(58) Field of Classification Search
CPC .................................................... A01N 43/16
See application file for complete search history.

(56) References Cited

U.S. PATENT DOCUMENTS

| | | | |
|---|---|---|---|
| 3,263,012 | A | 7/1966 | Nadler et al. |
| 4,320,140 | A | 3/1982 | Crounse et al. |
| 5,696,207 | A | 12/1997 | Vargo et al. |
| 5,698,207 | A | 12/1997 | Staats |
| 2013/0281913 | A1 | 10/2013 | Piergallini et al. |
| 2013/0323683 | A1 | 12/2013 | Piergallini et al. |
| 2015/0119788 | A1 | 4/2015 | Loupis et al. |
| 2015/0335904 | A1 | 11/2015 | Loupis et al. |
| 2016/0030564 | A1 | 2/2016 | Loupis et al. |
| 2016/0193338 | A1 | 7/2016 | Loupis et al. |
| 2016/0237097 | A1 | 8/2016 | Natarajan et al. |
| 2017/0064964 | A1 | 3/2017 | Bell et al. |

FOREIGN PATENT DOCUMENTS

| | | |
|---|---|---|
| CA | 2883717 A1 | 3/2014 |
| JP | S5639004 A | 4/1981 |
| JP | 2003277950 A | 10/2003 |
| JP | 2017071554 A | 4/2017 |
| WO | 0112181 A1 | 2/2001 |
| WO | 2012034032 A2 | 3/2012 |
| WO | 2013177674 A1 | 12/2013 |
| WO | 2014028011 A1 | 2/2014 |

OTHER PUBLICATIONS

Termir, Inc., PCT/US2018/041777 filed Jul. 12, 2018, "The International Search Report and Written Opinion of the International Searching Authority, or the Declaration", 18 pages, mailed Nov. 9, 2018.
European Patent Office in connection with PCT/US2018/041777 filed Jul. 12, 2018, "Extended European Search Report", 10 pages, mailed Mar. 5, 2021.
Kato et al., "Xanthene Dyes Induce Membrane Permeabilization of Bacteria and Erythrocytes by Photoinactivation", Photochemistry and Photobiology, vol. 88, pp. 423-431, 2012.
Korrapati et al., "Effect of Hofmeister series salts and BSA on fluorescein compounds", International Journal of ChemTech Research, vol. 8, No. 12, pp. 348-359, 2015.
Office Action in JP2020523686, mailed Aug. 2, 2022, 7 pages.
Yoshikawa et al., "Photodynamic action of fluorescein dyes in DNA-damage and in vitro inactivation of transforming DNA in bacteria," Mutation Research, vol. 56, 1978, pp. 359-362.
Liquido et al., "Light-Activated Toxicity of Phloxine B and Fluorescein in Methyleugenol to Oriental Fruit Fly, *Bactrocera dorsalis* (Hendel) (Diptera: Tephritidae), Males," ACS Symposium Series, Chapter 8, May 5, 1995, pp. 107-114.

*Primary Examiner* — Yong S. Chong
(74) *Attorney, Agent, or Firm* — McKee, Voorhees & Sease, PLC

(57) ABSTRACT

Provided are compositions and methods relating to antimicrobial compositions. In particular, the invention relates to antimicrobial compositions providing a xanthene dye and component that acts in synergy with the xanthene dye and methods of using antimicrobial compositions for treatment of biological tissues. In particular, the component acting in synergy with the xanthene dye is an organic dye, borate, an inorganic salt, and combinations thereof.

14 Claims, No Drawings

ANTIMICROBIAL COMPOSITIONS EFFECTIVE AGAINST BACTERIA AND FUNGUS

CROSS-REFERENCE TO RELATED APPLICATIONS

This application is a Continuation Application of PCT/US18/41777, filed Jul. 12, 2018, which claims priority to Provisional Application U.S. Ser. No. 62/531,528, filed on Jul. 12, 2017, and to Provisional Application U.S. Ser. No. 62/531,538, filed on Jul. 12, 2017, all of which are herein incorporated by reference in their entirety.

FIELD OF THE INVENTION

The invention relates generally to the field of antimicrobial compositions. In particular, the invention relates to antimicrobial compositions which contain a xanthene dye and component that acts in synergy with the xanthene dye and methods of using antimicrobial compositions for treatment of biological tissues. In particular, the component acting in synergy with the xanthene dye is an organic dye, borate, an inorganic salt, and combinations thereof.

BACKGROUND OF THE INVENTION

There is an ever-present need in industry to control infectious disease, particularly those caused by insects, pests, bacteria, viruses, fungi, etc., particularly in the industries of crop and livestock production, medical and health care for humans and animals, and environmental treatment such as bioremediation and water treatment. However, there is an additional concern of increased insecticidal, bacterial, and fungicidal resistance to currently available chemical control treatments found in insects, bacteria, and fungi, which decreases the effectiveness of the chemicals and places the crops and animals at risk for disease as well as placing an economic burden on growers, farmers, ranchers, manufacturers, and purchasers should the chemical control treatment be found to be ineffective after application. Traditional and currently available chemical control treatments have had some success in combatting resistance, however, there a need for effective broad-spectrum antimicrobial compositions which are not as susceptible to resistance.

Additionally, there is a need for medical and agricultural antimicrobials to be effective against both bacteria and fungus. Compounds such as xanthene dyes and phloxineB (PhlB) produce differing effects in bacterial and fungal species.

For bacteria, each of the members of the xanthene dyes family will have different Gram-positive (Gram(+)) bacteria LD50 concentrations; however, they are less effective against Gram-negative (Gram(−)) bacteria. Such relevant bacteria strains are dependent on the nature of the industry, but typically include: Gram-positive bacteria in the families of *Actinomyces, Basillus, Clostridium, Corynebacterium, Enterococcus, Gardenerella, Lactobacillus, Listeria, Mycobacterium, Mycoplasma, Norcardia, Propionibacterium, Stphylococcus, Streptococcus, Streptomyces*, etc.; and Gram-negative bacteria in the families of *Borellia, Bortadella, Burkholderia, Campylobacter, Chlamydia, Enterobacter, Eschericia, Fusobacterium, Heliobacter, Hemophilus, Klebsiella, Legionella, Leptospriria, Neisseria, Nitrobacter, Proteus, Pseudomonas, Rickettsia, Salmonella, Serratia, Shigella, Thiobacter, Treponema, Vibrio, Yersinia*, etc.

PhlB has been shown to control Gram(+) bacteria at millimolar to micromolar concentrations. Research with PhlB demonstrates it as an antibacterial agent for Gram(+) bacteria. However, PhlB on its own does not control Gram (−) bacteria. Many pathogenic or difficult to control bacteria in plants and animals are Gram(−). The central issue with PhlB in control of microbes with a Gram(−) type cell wall is with uptake. The dye must be able to pass through the cell wall to be active on the internal cell membranes and cell machinery of bacteria. There are some additives which have proven to be useful in facilitating the impact of halogenated xanthene dyes for Gram(−) bacteria control. These include cell wall degrading chemicals, chelation chemicals, or ultra-high pressure placed onto the target bacteria. Destabilizing the outer membrane will lead to more uptake of the dyes and to greater sensitivity of Gram(−) bacteria. These remedies, while functional, are not commercially useful or without toxicity issues. An additional issue for PhlB, and other xanthene dye control, are the wavelengths of light which the compounds must absorb, and the number/type of halogen atoms attached to the core molecule. Light passing through biological tissue, intensity of light (cloudy days), and the solution the dyes are in prior to cellular uptake will alter the photo-reaction(s) and subsequently the level of cellular damage the dye(s) can inflict on target organisms.

Bacteria control without both Gram(+) and Gram(−) control activity historically has not been worth developing for commercial use. For PhlB to be effective and commercially prudent, it would have to be enhanced to control bacteria and other microbes to a greater extent than currently available. To enhance the microbial control function of xanthene dyes, in particular PhlB, a component that acts in synergy for PhlB must be used as discovered by the inventors.

For fungus, for example, the free radicals and oxygen produced by the photodynamic action of PhlB and xanthene dyes reacts with biological cell membranes. Sites of unsaturation and lipids in microorganisms are degraded to photo-oxidation. The resulting impact of the free radicals and oxygen is cell and/or membrane damage, i.e., loss of internal and external membrane integrity. Conventional pharmacological, and some agricultural, fungicides target specific binding sites and enzymes of biochemical pathway in the target organism, which leads to resistance as the fungus mutates. This enzyme targeting also leads a conventional fungicide to be slow-acting and can allow for continued growth before control is achieved. Non-specific active site fungicides, used in agricultural environments, can be effective but toxic to the host organism and applicators. Targeting of a plant's systemic acquired immune response can work well as a prophylactic treatment but, do not reduce fungal load following an infection. Such relevant fungal strains are dependent on the nature of the industry, but typically include those in the genera of: *alternaria, botrytis, colletotrichum, erwinia, fusarium, gymnosporangium, monilinia, phragmidium, phytophthora, plasmodiophora, plasmopara, pythium, rhizoctonia, taphrina, ustilago, venturia*, and the like.

Historically, hydrophilic compounds and dyes, such as PhlB, are not common in conventional fungicides, as they have difficulty entering the fungi via the cell wall and fail to control the fungal infection. To enhance the microbial control function of xanthene dyes, in particular PhlB, a component that acts in synergy for PhlB must be used as discovered by the inventors.

There is a long-felt need in the art for development of antimicrobial compounds is needed to which must be fast acting, highly effective, less toxic, and have a reduced chance for development of antibiotic resistance. The present invention meets these needs.

SUMMARY OF THE INVENTION

Applicant has identified a novel antimicrobial composition comprising a xanthene dye in combination with one or more synergists of an organic dye, a borate, or an inorganic salt, and/or combinations thereof. According to an embodiment of the invention, the xanthene dye is a fluorescein, eosin, rhodamine, and/or combinations thereof. The component that acts in synergy with the xanthene dye is fluorescein (3',6'-dihydroxyspiro[2-benzofuran-3,9'-xanthene]-1-one), fluorescein isothiocynatate, NHS-fluorescein, carboxyfluorescein, carboxyfluorescein succinimidyl ester, pentafluorophenyl esters, tetrafluorophenyl esters, protected fluorescein compound, sodium borate, sodium tetraborate, disodium tetraborate, a salt of aluminum, ammonium, barium, beryllium, calcium, cesium, lithium, magnesium, potassium, rubidium, sodium, strontium, and combinations thereof. In a further embodiment of the invention, the xanthene dye and the component with acts in synergy with the xanthene dye are present in a ratio from about 0.001:1 to about 1:0.001. According to a still further embodiment, the composition further comprises at least one additional functional ingredient such as: extenders, solvents, spontaneity promoters, carriers, emulsifiers, dispersants, frost protectants, thickeners and adjuvants, and insect food sources.

In another embodiment of the invention, a method of treating and/or preventing bacterial and/or fungal infection, is included herewith, the method comprising: obtaining or forming an antimicrobial composition comprising a xanthene dye and at least one component that acts in synergy therewith, selected from an organic dye, a borate, an inorganic salt, and/or combinations thereof and thereafter contacting a target with said composition. In a preferred embodiment, the target is a plant and/or its root system, the surface of a fruit, vegetable, grain, or other food surface, animal tissue, or water. In a still further embodiment of the invention, the method further comprises providing the compositions of the invention via any of spraying, daubing, coating, painting, fogging, flooding, mixing, coating, and combinations thereof. In a further embodiment, the method comprises a diluting step, wherein the compositions of the invention are diluted to a desired treatment concentration. In a further embodiment, the method allows for the compositions to contact the target for a defined period of time. In a still further embodiment, the method comprises rinsing the composition from the target.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

DETAILED DESCRIPTION OF THE INVENTION

The present invention relates generally to the field of antimicrobial compositions. In particular, the invention relates to antimicrobial compositions which contain a xanthene dye in synergistic combination with an organic dye, a borate, an inorganic salt, or combinations thereof and methods of using antimicrobial compositions. The compositions and methods according to the present invention have many advantages over existing antimicrobial compositions, including, for example, enhancing the control range of the dye for microbes, such as bacteria and/or fungus while reducing the dose of the dye, increasing control levels, and lowering the time needed for control.

The embodiments of this invention are not limited to particular compositions or methods, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to moles, reduction, mass, weight, and the like. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulthydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is achieved with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthroscopes) and related equipment, and the like, or combinations thereof.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

For the purpose of this patent application, successful microbial reduction is achieved when the microbial populations are reduced by at least about 10%, by at least about 20%, by at least about 30%, by at least about 40%, at least about 50%, or by significantly more than is achieved by contact. Larger reductions in microbial population provide greater levels of protection.

The term "plant" is intended to include a whole plant, any part of a plant, a seed, a fruit, propagules and progeny of a plant. Crop plants and agricultural plants are those of economic importance for human or animal food production or for animal fodder production and includes primarily citrus but can include grains, fruits and vegetables as well as grasses. Horticultural plants include those for turfgrass, windbreaks and landscaping and include ornamental plants such as flowers, shrubs, vines and the like.

As used herein, the term "plant tissue" includes differentiated and undifferentiated tissues of plants including those present in roots, shoots, leaves, pollen, seeds and tumors, as well as cells in culture (e.g., single cells, protoplasts, embryos, cellus, etc.). Plant tissue may be in planta, in organ culture, tissue culture, or cell culture.

As used herein, "target" broadly refers to any biological or hard surface which may benefit from bacterial reduction and/or treatment.

As used herein, "treating" or "treatment" refers to the use of the compositions of the invention to eradicate, reduce, remove, heal, or cure a plant or animal of disease, or to remove, clean, or sanitize a hard surface of bacteria.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and may be used interchangeably with either bactericidal, or fungicidal; and the later, microbistatic and may be used interchangeably with either bacteriostatic, or fungistatic. A sanitizer and a disinfectant are, by definition, agents which provide antimicrobial or microbiocidal activity. In contrast, a preservative is generally described as an inhibitor or microbistatic composition.

As used herein, the term "substantially free" refers to compositions completely lacking the component or having such a small amount of the component that the component does not affect the performance of the composition. The component may be present as an impurity or as a contaminant and shall be less than 0.5 wt. %. In another embodiment, the amount of the component is less than 0.1 wt. % and in yet another embodiment, the amount of component is less than 0.01 wt. %.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

The terms "water soluble" and "water dispersible" as used herein in reference to polymers, means that the polymer is soluble or dispersible in water in the inventive compositions. In general, the polymer should be soluble or dispersible at 25° C. at a concentration of 0.0001% by weight of the water solution and/or water carrier, preferably at 0.001%, more preferably at 0.01% and most preferably at 0.1%.

The term "weight percent," "wt. %," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt. %," etc.

The methods, systems, apparatuses, and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Compositions

An embodiment of the invention is found in antimicrobial compositions useful for the control of bacteria and/or fungi present in plant growth, livestock facilities, and manufacturing systems. The antimicrobial compositions according to the present invention include a xanthene dye and a component which acts in synergy with the xanthene dye, such as an organic dye, borate, and/or inorganic salt. Optionally, the antimicrobial compositions can include additional functional ingredients which may be present dependent on the desired properties of the antimicrobial compositions.

It is unexpectedly found that the addition of a component to a xanthene dye according to the present invention enhances the control range of the dye for bacteria, fungi, and microbes while reducing the dose of the dye, increasing control levels, and lowering the time needed for control by generating synergy between said component and the xanthene dye. The addition of a component to the dye allows for unexpected and superior control of bacterial, both Gram-positive and Gram-negative bacteria, and fungi at lower molar dosages. The formulation(s) have a unique ability to move in vascular systems of animals, fungi, and plants. This transport facilitates deposition of the dyes into different regions of the organism. Antibiotics can be difficult to move around organisms, particularly in plants. The speed of control for this formulation(s) is also unique. Activated by sunlight, ambient electric light, and flux pulses, the dye will begin to photo-oxidize within the target microbe. Control using these formulations can be in hours, not in the weeks or months it takes for control using antibiotics. It should also be noted that the use of traditional antibiotics in agriculture is being phased out, as a precaution for antibiotic resistance. These unique chemical mixtures offer a unique opportunity for microbial control with a new mode of action, with less chance for resistance development that with traditional antibiotics.

Xanthene Dye

According to an embodiment of the invention, the antimicrobial composition includes xanthene dye, xanthene derivative dye, and combinations thereof. It is to be understood that any suitable xanthene dye or suitable xanthene derivative dye may be used in the antimicrobial composition. In particular, suitable xanthene derivative dyes may include, but are not limited to, xanthene dyes which maintain the general structure of the xanthene dye but have substituted halogen or R-groups as various or multiple locations.

Both cationic and anionic xanthene dyes are known to be efficient fluorescent compounds whose colors are controlled by the functional groups on the xanthene moiety.

Xanthene (9H-xanthene, 10H-9-oxaanthracene) is an organic, heterocylic compound that produces a yellow dye. Derivatives of xanthene include fluoresceins, eosins, rhodamines, and the like.

Fluoresceins, as shown in Formula I, include 3',6'-dihydroxyspiro[isobenzofuran-1(3H),9'-[9H]xanthen]-3-one, fluorescein isothiocynatate, NHS-fluorescein, carboxyfluorescein, carboxyfluorescein succinimidyl ester, pentafluorophenyl esters, tetrafluorophenyl esters, protected fluorescein compounds such as 6-FAM phosphoramidite, phloxineB, and the like. In a preferred embodiment, the xanthene dye is phloxineB (PhlB), which is identified principally as the disodium salt of 2',4',5',7'-tetrabromo-4,5,6,7-tetrachlorofluorescein.

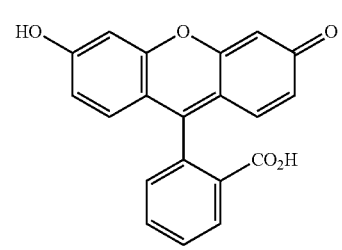

(I)

Eosins are fluorescent acid compounds, as depicted by Formula II, which bind to and form salts with basic, or eosinophilic, compounds like proteins containing amino acids residues. Suitable eosins include eosin Y and eosin B.

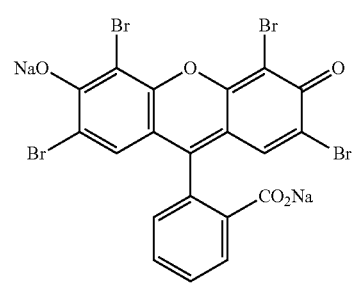

(II)

Rhodamines, as shown in Formula III, are fluorone dyes and include suitable compounds such as rhodamine B, rhodamine 6G, rhodamine 123, acrboxytetramethylrhodamine (TAMRA), tetramethylrhodamine (TMR) and its isothiocyanate derivative (TRITC) and, sulforhodamine 101 (and its sulfonyl chloride form Texas Red) and Rhodamine Red. TRITC is the base rhodamine molecule functionalized with an isothiocyanate group (—N═C═S), replacing a hydrogen atom on the bottom ring of the structure. This derivative is reactive towards amine groups on proteins inside cells. A succinimidyl-ester functional group attached to the rhodamine core, creating NHS-rhodamine, forms another common amine-reactive derivative. Other derivatives of rhodamine include newer fluorophores such as Alexa 546, Alexa 555, Alexa 633 (available from Thermo Fisher Scientific); DyLight 550 and DyLight 633 (available from Thermo Fisher Scientific); HiLyte fluor 555, HiLyte 59 (available from AnaSpec).

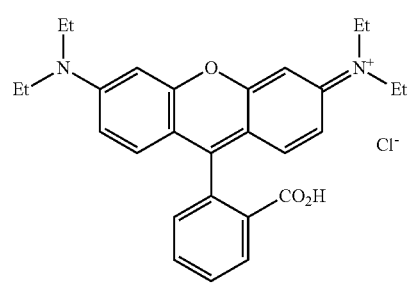

(III)

Other suitable xanthene dyes are defined by Formulas (IV)-(XXIX):
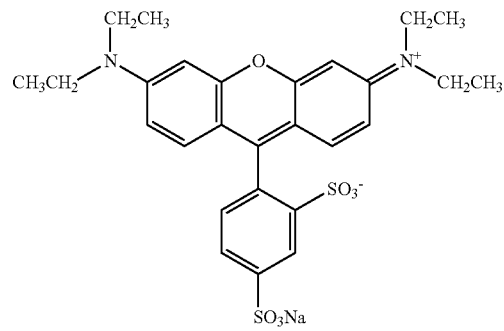
(IV)
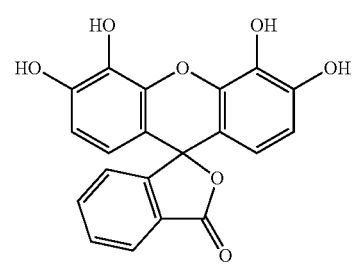
(V)
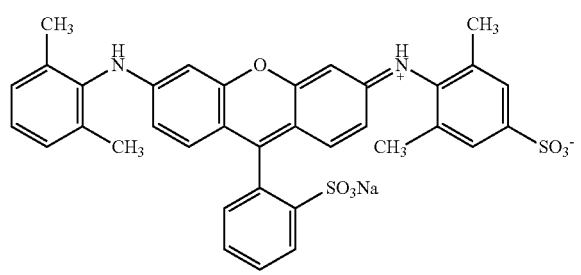
(VI)
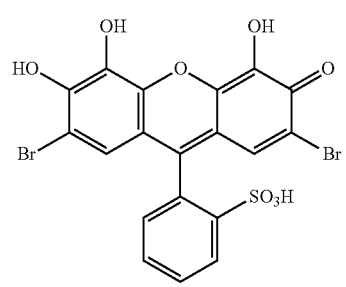
(VII)
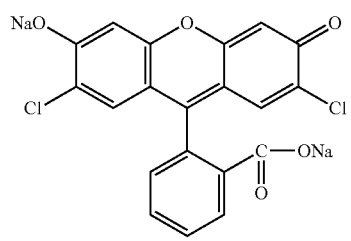
(VIII)
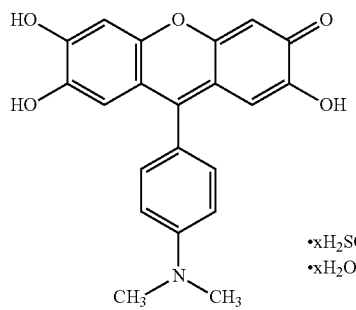
(IX)
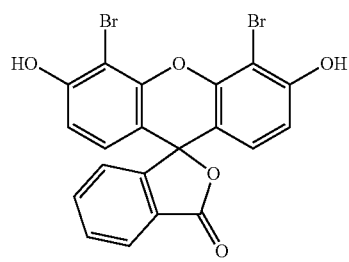
(X)
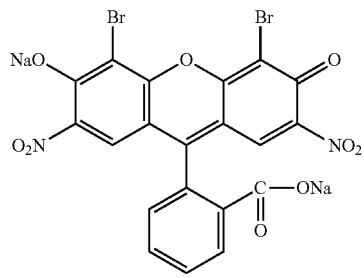
(XI)
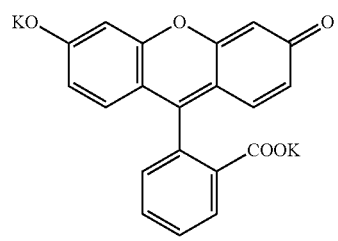
(XII)
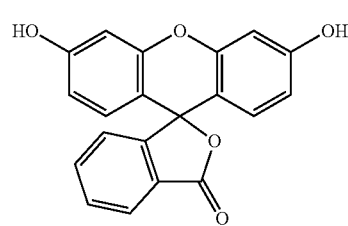
(XIII)
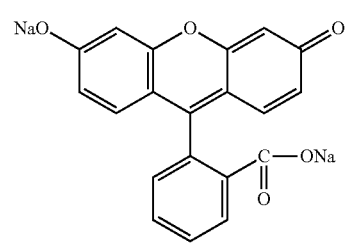
(XIV)

-continued
(XV)
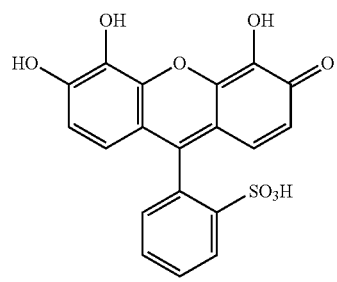
(XVII)
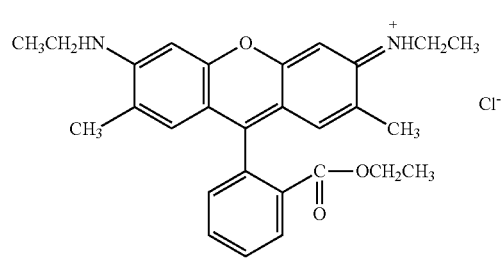
(XVIII)
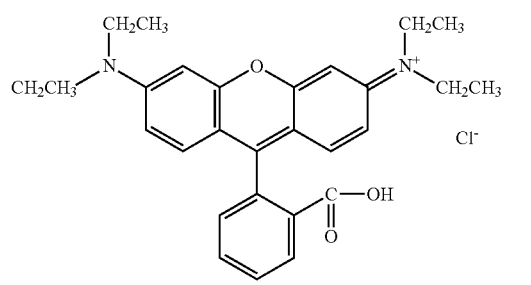
(XIX)
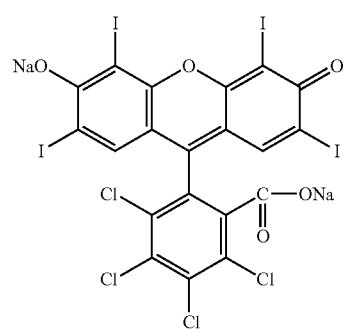
(XX)
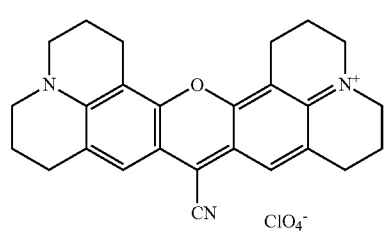
(XXI)
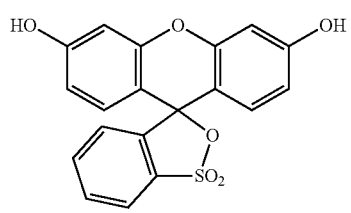
-continued
(XXII)
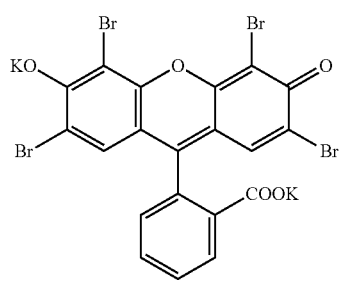
(XXIII)
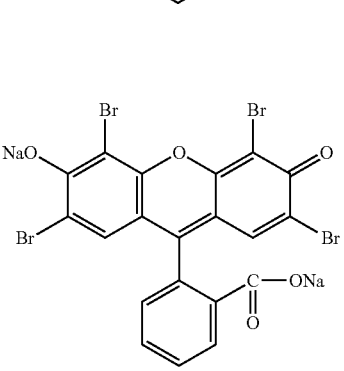
(XXIV)
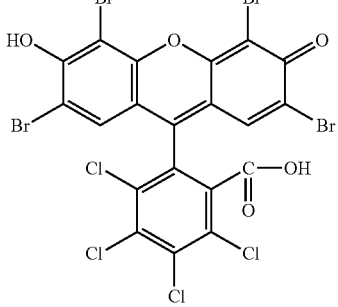
(XXV)
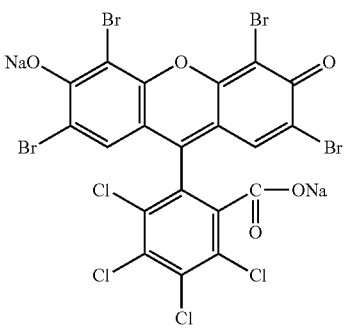
(XXVI)
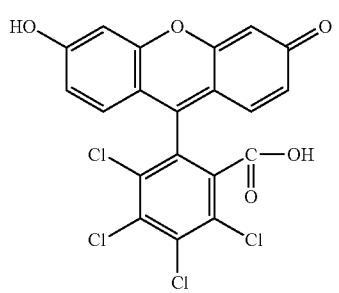

-continued

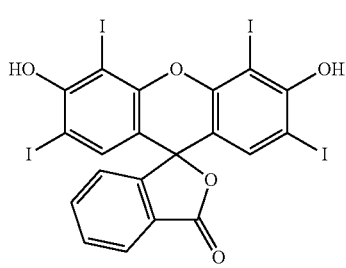

(XXVII)

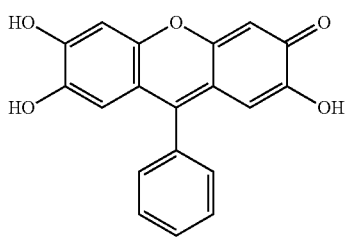

(XXVIII)

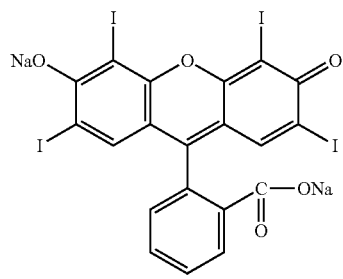

(XXIX)

In an aspect of the invention, the antimicrobial compositions contain a ratio of organic dye, borate, inorganic salt, or combination thereof to xanthene dye from about 0.001:1 to about 1:0.001, from about 0.005:1 to about 1:005, from about 0.05:1 to about 1:0.05; from about 0.1:1 to about 1:0.1, and from about 0.5:1 to about 1:0.5.

In a further aspect of the invention, the xanthene dye is present in compositions in the amount of about 0 wt. % to about 50 wt. %, more preferably from about 0 wt. % to about 20 wt. %, more preferably from about 0.1 wt. % to about 10 wt. %, and even more preferably from about 0.1 wt. % to about 0.5 wt. %

Organic Dye

The antimicrobial compositions include at least one compound providing synergistic control when present in combination with the xanthene dye. In an aspect of the invention, this is an organic dye, borate, inorganic salt, and combinations thereof.

In an embodiment of the invention, the compound providing synergistic control in combination with a xanthene dye is at least one organic dye generated from natural, plant, or synthetic sources. Any suitable organic dye may be used in compositions according to the invention. Such natural or plant dyes come from roots, berries, bark, leaves, wood, fungi, lichens, and the like. Further, synthetic reactions may be utilized to produce suitable organic dyes. Such techniques and suitable organic dyes are disclosed in Zollinger, *Color Chemistry: Syntheses, Properties, and Applications of Organic Dyes and Pigments*, Wiley (2003), which is hereby incorporated by reference in its entirety.

In a preferred embodiment of the invention, the organic dye is fluorescein (3',6'-dihydroxyspiro[2-benzofuran-3,9'-xanthene]-1-one), a fluorescein derivative, and combinations thereof. Such derivatives include fluorescein isothiocynatate, NHS-fluorescein, carboxyfluorescein, carboxyfluorescein succinimidyl ester, pentafluorophenyl esters, tetrafluorophenyl esters, protected fluorescein compounds such as 6-FAM phosphoramidite, and the like.

In an aspect of the invention, at least one organic dye is included in the antimicrobial composition. In a further aspect, at least two, at least three, or at least four organic dyes are included in the antimicrobial composition.

In an aspect of the invention, where the component which acts in synergy with the xanthene dye is an organic dye, the antimicrobial compositions contain at least 50 micromoles, preferably at least 60 micromoles, and more preferably at least 62 micromoles.

In an aspect of the invention, the organic dye is present in compositions in the amount of about 0 wt. % to about 99 wt. %, from about 0 wt. % to about 80 wt. %, from about 0 wt. % to about 60 wt. %, from about 0 wt. % to about 35 wt. %, from about 0 wt. % to about 10 wt. %, and from about 0 wt. % to about 5 wt. %.

Inorganic Salt

In an embodiment of the invention, the compound providing synergistic control in combination with a xanthene dye is at least one inorganic salt. Any suitable inorganic salt may be used in compositions according to the invention. In an aspect of the invention, the inorganic salt is a salt of aluminum, ammonium, barium, beryllium, calcium, cesium, lithium, magnesium, potassium, rubidium, sodium, strontium, and the like, and combinations thereof. Other suitable inorganic salts include aluminum potassium sulfate, ammonium magnesium phosphate, ammonium sodium phosphate, lithium potassium acetyl phosphate, manganese (II) chloride, manganese (II) sulfate, scandium (III) chlorine hydrogen. In an aspect of the invention, the inorganic salt is ammonium acetate, ammonium bicarbonate, ammonium bromide, ammonium chloride, ammonium fluoride, ammonium formate, ammonium hexafluorophosphate, ammonium hydrogensulfate, ammonium iodide, ammonium nitrate, ammonium phosphate, ammonium sulfamate, ammonium sulfate, ammonium sulfide, ammonium sulfite, ammonium thiosulfate, ammonium trifluroacetate, ammonium trifluoromethanesulfate, hydroxylammonium nitrate. In a preferred embodiment of the invention, the inorganic salt is ammonium sulfate.

In an aspect of the invention, at least one inorganic salt is included in the antimicrobial composition. In a further aspect, at least two, at least three, or at least four inorganic salts are included in the antimicrobial composition.

In an aspect of the invention, the antimicrobial compositions contain at least 2 millimoles, preferably at least 5 millimoles, and more preferably at least 10 millimoles.

In an aspect of the invention, the inorganic salt is present in composition in the amount of 0 wt. % to about 100 wt. %, from about 30 wt. % to about 100 wt. %, from about 50 wt. % to about 100 wt. %, from about 70 wt. % to about 100 wt. %, and from about 90 to about 100 wt. %.

Borate

In an aspect of the invention, the compound providing synergistic control in combination with a xanthene dye is a borate, a borate derivative, and combinations thereof. A borate is classified as boron-containing oxyanions, tetrahedral boron anions, and/or compounds containing borate anions. In simplest form, a borate contains the orthoborate ion $BO_3^{3-}$. Suitable borate compounds include borate salts, borate esters, and the like. Suitable compounds include, but are not limited to, borate ore, trimethyl borate, triisopropyl borate, triethyl borate, triphenyl borate, zinc borate, tributyl borate, triethanolamine borate, tris(trimethylsilyl) borate, tri-tert-butyl borate, lanthanum borate, phenylmercuric borate, trihexadecyl borate, yttrium borate, lithium tetrakis(pentafluorophenyl)borate ethyl etherate, potassium tetrakis(4-chlorophenyl) borate, sodium tetra(p-tolyl)borate, sodium tetrakis(4-fluorophenyl)borate dehydrate, tetradodecylammonium tetrakis(4-chlorophenyl)borate, hydrogen [4-di-tert-butylphosphino-2,3,5,6-tetrafluorophenyl]hydrobis(2,3,4,5,6-pentafluorophenyl)borate, sodium tetrakis(1-imidazolyl)borate, potassium tetrakis(4-tert-butylphenyl) borate, potassium tetrakis(4-biphenylyl)borate, potassium tetrakis(2-thienyl)borate, lanthanum calcium borate, lithium bis(oxalate)borate, tris(2,2,2-triflourorethyl)borate, yttrium aluminum borate, bis(1,5-cyclooctadiene)rhodium(I) tetrakis[bis(3,5-trifluoromethyl)phenyl]borate, sodium tetrakis[3,5-bis(trifluoromethyl)phenyl]borate, sodium tetrakis[3,5-bis(1,1,1,3,3,3-hexafluoro-2-methoxy-2-propyl)phenyl] borate trihydrate, Potassium trifluoro[(pyrrolidin-1-yl) methyl]borate, sodium borate, sodium tetraborate, disodium tetraborate, 2-Aminoethyldiphenyl borate, sodium tetraphenyl borate, 1-Butyl-1-methylpyrrolidinium bis[oxalate(2-) O,O']borate, sodium tetraborate decahydrate, borax, calcium metaborate, potassium tetraphenylborate, 2-aminoethyl diphenylborate, potassium 2-naphtalenetriflurorborate, potassium allyltrifluroborate, potassium 1-methyl-1H-pyrazole-5-trifluoroborate, potassium quinoline-6-trifluoroborate, and the like. In a preferred embodiment of the invention, the borate is sodium borate, sodium tetraborate, or disodium tetraborate, or combinations thereof.

In an aspect of the invention, at least one borate is included in the antimicrobial composition. In a further aspect, at least two, at least three, or at least four borates are included in the antimicrobial composition.

In an aspect of the invention, where the component which acts in synergy with the xanthene dye is an inorganic salt, the antimicrobial compositions contain at least 75 millimole, preferably at least 85 millimole, and more preferably at least 90 millimole.

In an aspect of the invention, the borate is present in composition in the amount of 0 wt. % to about 100 wt. %, from about 30 wt. % to about 100 wt. %, from about 50 wt. % to about 95 wt. %, from about 70 wt. % to about 95 wt. %, and from about 90 to about 95 wt. %.

Additional Functional Ingredients

In embodiments of the invention, additional ingredients can be included in the antimicrobial compositions. The additional ingredients provide desired properties and functionalities to the compositions. For the purpose of this application, the term "functional ingredient" includes a material that provides a beneficial property in a particular use. Some particular examples of functional materials are discussed in more detail below, although the particular materials discussed are given by way of example only, and that a broad variety of other functional ingredients may be used. For example, many of the functional materials discussed below relate to materials used in antimicrobial applications, specifically plant treatment applications.

However, other embodiments may include functional ingredients for use in other applications. One aspect of the present invention is to provide a composition as described above that can be used as a feeding source and injected into plants, or added to create an alternate feeding source, additionally comprising at least one auxiliary selected from the group consisting of surfactants, antibacterial components, extenders, solvents, spontaneity promoters, carriers, emulsifiers, dispersants, frost protectants, sun protectants, thickeners and adjuvants. Those compositions are referred to as formulations and may be added to a food source for the insects.

Accordingly, in one aspect of the present invention such formulations, and application forms prepared from them, are provided as crop protection agents and/or pesticidal agents, such as drench, drip and spray liquors, comprising the composition of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers-173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as surfactants, antibacterial components, extenders, solvents, spontaneity promoters, carriers, emulsifiers, dispersants, frost protectants, sun protectants, biocides, thickeners and/or other auxiliaries, such as adjuvants, for example. An adjuvant in this context is a component which enhances the effect of the formulation, without the component itself producing the desired effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Auxiliaries

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Extenders

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Solvents and Carriers

In principle, it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are, in particular, for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Emulsifiers, Foam-Formers, Dispersants, Wetting Agents

Examples of emulsifiers and/or foam-formers, dispersants or wetting agents having ionic or nonionic properties, or mixtures of these surface-active substances, are xanthan gum, guar derivatives, salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors, and methylcellulose. The presence of a surface-active substance is advantageous if one of the active compounds and/or one of the inert carriers is not soluble in water and if application takes place in water.

Dyes

Further dyes that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Retention Promoters

Suitable retention promoters include all those substances which reduce the dynamic surface tension, such as dioctyl sulphosuccinate, or increase the viscoelasticity, such as hydroxypropylguar polymers, for example.

Penetrants

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (I5), or ammonium and/or phosphonium salts such as ammonium sulphate or diammonium hydrogen phosphate, for example.

The active compound content of the application forms (crop protection products) prepared from the formulations may vary within wide ranges. The additional functional ingredients of the application forms may be situated typically between about 0.01 wt. % and about 95 wt. %, between 0.01 wt. % and 50 wt. % by weight, between 0.01 wt. % and about 25 wt. %, and between about 0.01 wt. % and 15 wt. %, depending on the desired use and function of the antimicrobial composition.

Surfactants

In some embodiments, the compositions of the present invention optionally include a surfactant. Surfactants suitable for use with the compositions of the present invention include, but are not limited to, nonionic surfactants, anionic surfactants, and amphoteric surfactants. In a preferred embodiment of the invention, the optional surfactant is a nonionic surfactant. Without seeking to be limited to a particular theory of the invention, the presence of a nonionic surfactant assists in uptake of the compositions according to the invention.

Nonionic Surfactants

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties. Useful nonionic surfactants include:

Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available from BASF Corp. One class of compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Another class of compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Lutensol™, Dehydol™ manufactured by BASF, Neodol™ manufactured by Shell Chemical Co. and Alfonic™ manufactured by Vista Chemical Co.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Disponil or Agnique manufactured by BASF and Lipopegi™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty esters or acylated carbohydrates to compositions of the present invention containing amylase and/or lipase enzymes because of potential incompatibility.

Examples of nonionic low foaming surfactants include:

Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

The alkylphenoxypolyethoxyalkanols of U.S. Pat. No. 2,903,486 issued Sep. 8, 1959 to Brown et al. and represented by the formula

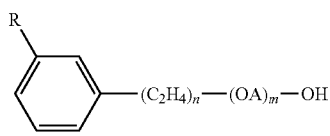

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkylene oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $YRC_3H_6O_n (C_2H_4O)_mH$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n (C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Fatty acid amide surfactants suitable for use the present compositions include those having the formula: $R_6CON (R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or —$(C_2H_4O)_xH$, where x is in the range of from 1 to 3.

A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}$—$(PO)_sN$-$(EO)_tH$, $R^{20}$—$(PO)_sN$-$(EO)_tH(EO)_uH$, and $R^{20}$—$N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}$—$(PO)_V$—$N$ $[(EO)_wH]$ $[(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonici™ PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface-active agents are another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

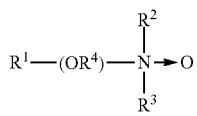

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water-soluble phosphine oxides having the following structure:

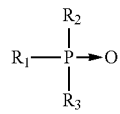

wherein the arrow is a conventional representation of a semi-polar bond; and, $R_1$ is an alkyl, alkenyl or hydroxyalkyl moiety ranging from 10 to about 24 carbon atoms in chain length; and, $R_2$ and $R_3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water-soluble sulfoxide compounds which have the structure:

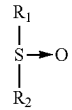

wherein the arrow is a conventional representation of a semi-polar bond; and, $R_1$ is an alkyl or hydroxyalkyl moiety of about 8 to about 28 carbon atoms, from 0 to about 5 ether linkages and from 0 to about 2 hydroxyl substituents; and $R_2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

Anionic Surfactants

Also useful in the present invention are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionics are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, sulfonated fatty acids, such as sulfonated oleic acid, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R—O—(CH_2CH_2O)_n(CH_2)_m—CO_2X \quad (3)$$

in which R is a $C_8$ to $C_{22}$ alkyl group or

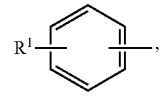

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

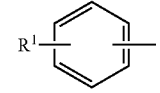

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

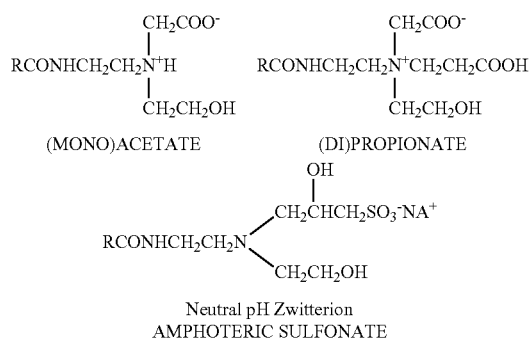

(MONO)ACETATE  (DI)PROPIONATE

Neutral pH Zwitterion
AMPHOTERIC SULFONATE wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—CH$_2$—CH$_2$—N$^+$(CH$_2$—CH$_2$—CO$_2$Na)$_2$—CH$_2$—CH$_2$—OH or $C_{12}$-alkyl-C(O)—N(H)—CH$_2$—CH$_2$—N$^+$(CH$_2$—CO$_2$Na)$_2$—CH$_2$—CH$_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated by reference in their entirety.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

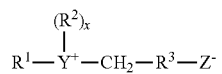

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

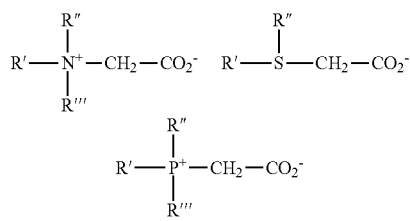

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+ R^2SO^{3-})$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Buffers

Any of the commonly known buffers compatible with other components may be used, examples of which include biological buffers, trizma buffer, phosphate buffers, citric acid buffer solutions, sodium acetate-acetic acid buffer solution, sodium phosphate buffers, imidazole-hydrogen chloride buffers, sodium carbonate-sodium bicarbonate buffers, and the like. In a further aspect of the disclosure, any suitable buffer may be used within a useful pH of 5-9, more preferably 6-8, and more preferably about 7.

Light Reducing Agents

In an aspect of the disclosure, compositions include a light reducing agent, also known as an anti-UV compound. The addition of such compounds slow the action of the active ingredients and promote better movement of the compositions throughout the plant and/or organism, thus increasing the effectiveness of the compositions according to the disclosure. Suitable compounds include, for example, p-Aminobenzoic acid, padimate O, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule, titanium dioxide, zinc oxide, 4-methylbenzylidene camphor, bisoctrizole, anisotraizine, tris-biphenyl triazine, bisimidazylate, drometrizole trisiloxane, benzophenone-9, octyl traizone, diethylamino hydroxybenzoyl butamido triazone, dimethico-diethylbenzalmalonate, isopentyl-4-methoxycinnamate, combinations thereof, and the like.

Antimicrobial Components

Antimicrobial agents are chemical compositions that are used to prevent microbiological contamination and deterioration of products, materials, mediums (such as water process streams) and systems. Antimicrobial agents and compositions are used, for example, as disinfectants or sanitizers in association with hard surface cleaning, food preparation, animal feed, cooling water, hospitality services, hospital and medical uses, pulp and paper manufacturing, cleaning textiles, and water processing. Any suitable antibacterial component may be used including, but not limited to, alcohols, aldehydes, halogen-releasing compounds, peroxides, gaseous substances, anilides, biguanides, bisphenols, halophenol, phenols, cresols, quaternary ammonium compounds, derivatives thereof, and combinations thereof.

Preventing or Ameliorating Bacterial or Fungal Infection

The present disclosure relates, in some embodiments, to compositions, systems, and methods for preventing, ameliorating, and/or treating a plant disease (e.g., a citrus disease, blight, mildew, etc.) and/or at least one symptom of a plant disease. The compositions according to the claimed invention provide disease treatment, prevention, and amelioration when applied to diseased biological tissue, wherein the disease is caused by bacteria, viruses, fungi, insects, pests, etc.

The present invention contemplates a concentrate composition of the present invention which is diluted to a use solution prior to its utilization as an antimicrobial treatment composition. Exemplary embodiments in terms of weight percentages of the antimicrobial composition are shown in Table 1.

TABLE 1

| Component | First Embodiment | Second Embodiment | Third Embodiment |
|---|---|---|---|
| Xanthene Dye Components Acting in Synergy | 0.01-50 wt. % | 0.05-20 wt. % | 0.1-10 wt. % |
| Organic Dye | 0.01-60 wt. % | 0.05-35 wt. % | 0.1-10 wt. % |
| Borate | 50-95 wt. % | 70-95 wt. % | 90-95 wt. % |
| Inorganic Salt | 50-100 wt. % | 70-100 wt. % | 90-100 wt. % |
| Additional Functional Ingredient | 0.01-95 wt. % | 0.01-50 wt. % | 0.01-25 wt. % |

The invention contemplates a composition which is effective for bacterial and fungal control at highly variable pH ranges. In an embodiment of the invention, the composition is effective for bacterial and/or fungal control over the entire pH range, i.e., 0-14. In a further embodiment of the invention, the composition is effective over a pH range of 2-12, more preferably from 2-10, more preferably from 4-10, and more preferably from 6-8.

The compositions of the invention can be applied to biological tissue, specifically plant and animal tissue in a variety of techniques. The aqueous solution can be sprayed, painted, daubed, fogged, or flooded onto or into the plant, the plant hydroponic substrate, the agricultural soil, or onto the body of a livestock animal. Alternatively, the compositions can be incorporated in animal feed via spraying, mixing, coating, or slurry. Additionally, the compositions can be solidified and contacted with the biological tissue of a livestock animal via ingesting.

In an embodiment of the invention, the target is a plant and/or its root system. In a further embodiment of the invention, the target is the surface of a fruit, vegetable, or grain, or other food surface. In a further embodiment of the invention, the target is animal tissue. In a still further embodiment of the invention, the target is water. In a still further embodiment, the target is an industrial food processing and/or manufacturing hard surface.

Examples of a plant disease are generally classified by the affected area and can be categorized by seed rot diseases, seedling diseases, root diseases, stem diseases, stalk rot diseases, ear rot diseases, foliar diseases, diseases causing excess greening as in fruit. Such examples include without limitation: nematode disease variants, rust disease variants, smut disease variants, wilt disease variants, spot disease variants, blight disease variants, mildew disease variants, rot disease variants, pustule and mottle disease variants, mold disease variants, citrus greening disease variants. According to some embodiments, preventing, ameliorating, and/or treating a plant disease and/or at least one symptom of a plant disease may comprise treating and/or curing one or more devastating bacterial and/or fungal diseases of plants.

The present disclosure also relates, in some embodiments, to compositions, systems, and methods for preventing, ameliorating, and/or treating livestock either internally or externally. For example, a method may comprises treating the animal skin via spraying, coating, or washing with the compositions according to the present invention.

The present disclosure also relates, in some embodiments, to compositions, systems, and methods for preventing, ameliorating, and/or treating a manure treatment facility, manure storage facility, livestock confinement, animal rearing operation facility, or waste water treatment facility. For example, a method may comprise treating the facility's surfaces via spraying, coating, depositing with the compositions according to the present invention.

The present disclosure also relates, in some embodiments, to compositions, systems, and methods for preventing, ameliorating, and/or treating industrial food processing and/or manufacturing facilities. In particular, the present disclosure relates to the treatment of industrial food processing and/or manufacturing facilities which handle agricultural inputs which are susceptible to bacterial and/or fungal infection including, but not limited to, grains, fruits, vegetables, dairy products, meat products, and animal products.

The compositions of the invention can be used for a variety of domestic or industrial applications, e.g., to reduce microbial or viral populations on a surface or object or in a body or stream of water. The compounds can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compounds can be employed as a foaming or non-foaming environmental sanitizer or disinfectant.

The compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, lubricants, rinse aids, 2-in-1 and/or 3-in-1 products, such as insecticide/cleaner/sanitizer, 3-sink applications, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people.

In some aspects, the compositions of the present invention can be employed for reducing the population of pathogenic microorganisms, such as pathogens of humans, animals, and the like. The compounds exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. Compositions of the present invention can reduce the population of microorganisms on skin or other external or mucosal surfaces of an animal. In addition, the present compounds can kill pathogenic microorganisms that spread through transfer by water, air, or a surface substrate. The compositions need only be applied to the skin, other external or mucosal surfaces of an animal water, air, or surface.

According to a method of the invention, the method for preventing, ameliorating, and/or treating includes forming a composition according to the invention and contacting said cleaning solution with a target. The method can optionally further comprise diluting a composition according to the invention to a desired concentration. The method can optionally further comprise allowing contact to persist for a desired time period. The method can optionally further comprise a rinse step. The method can optionally further comprise contacting via any of spraying, daubing, coating, painting, fogging, flooding, mixing, coating, and the like, and combinations thereof.

All references and patent documents cited herein reflect the level of skill in the relevant arts and are incorporated by reference in their entireties to the extent there is no inconsistency with the present disclosure. The examples provided herein are for illustrative purposes and are not intended to limit the scope of the invention as claimed. Any variations in the exemplified compositions, plants and methods which occur to the skilled artisan are intended to fall within the scope of the present invention.

EXAMPLES

Embodiments of the present invention are further defined in the following non-limiting Examples. It should be understood that these examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following Examples are provided herein:
Meuller Hinton Broth
*Rhizobium radiobacter* ATCC 700691 Gram(−) Bacteria
*Bacillus subtilis* ATCC 15841 Gram(+) Bacteria
*Ralstonia insidiosa* ATCC 49129 Gram(−) Bacteria
*Stenotrophomonas maltophilia* ATCC 13637 Gram(−) Bacteria
*Aspergillus brasiliensis* AATCC 6275
*Alternaria alternate* ATCC 66981
*Curvularia lunata* ATCC 12017
*Candida albicans* ATCC 10231

Example 1

Tests are conducted according to the 2015 Clinical and Laboratory Standards Institute Method M07-A10: Methods for dilution antimicrobial susceptibility tests for bacteria that grow aerobically. Sterile 96-well microplates are prepared with Meuller Hinton Broth containing varying amounts of test compounds in each well (100 μL per well). Then according to the CLSI M07-A10 microdilution assay, a row with a 2-fold serial dilution series with 10 different concentrations of the test compound are prepared along with three replicate rows for each combination of test organism and test compound. According to the CLSI M07-A10 microdilution combination (checkerboard) assay, an 8×8 well matrix containing two 2-fold serial dilution series of two test compounds arranged perpendicular to one another so that each concentration of compound 1 is prepared once with each combination of compound 2. One column with a 2-fold serial dilution series with 8 different concentrations of test compound 1 is prepared along with one column with a 2-fold serial dilution series with 8 different concentrations of test compound 2. One microplate for each combination of test organism and pair of test compounds is prepared in addition to a cell suspension of each test microorganism equivalent to a 0.5 McFarland turbidity standard using fresh isolated colonies grown on Meuller Hinton Agar. Each cell suspension is diluted in a 1:20 ratio in Meuller Hinton Broth and the microplate is inoculated by adding add 10 μL to each well. Microplates then incubate according to CLSI M07-A10.

Microplates are read and data was interpreted according to the following procedure: The minimum inhibitory concentration (MIC) is the minimum concentration of the test compound needed to cease growth of the organism, it encompasses microbe death as well as microbe loss of the ability to divide and grow. Supplemental light was used during the 24-hour incubation period. Light intensity ranged from 1259 and 4203 lux.

Results are shown in Tables 2-5 below. Reduced PhlB as shown in the tables indicates the fraction by with a traditional dosage of PhlB is reduced through the synergy exhibited by the addition of the described components of the invention.

TABLE 2

*Bacillus subtilis* ATCC 15841
MIC at 24 hours in Light

|  |  | PHL B(uM) | Molar ratio | Reduced PhlB |
|---|---|---|---|---|
| Fluorescein(uM) |  |  |  |  |
| Trial 1 | 62.5 | 0.49 |  |  |
| 1 | 62.5 | 0.03 | 0.00048 | 1/16 |
| 2 | 62.5 | 0.06 | 0.00096 | 1/8 |
| 3 | 62.5 | 0.12 | 0.00192 | 1/4 |
| 4 | 62.5 | 0.24 | 0.00384 | 1/2 |
| 5 | 62.5 | 0.49 | 0.00784 |  |
| 6 | 0.98 | 0.98 | 1 |  |
| 7 | 0.49 | 1.95 | 3.979591837 |  |
| 8 | 0.49 | 3.9 | 7.959183673 |  |
| NaTetraBorate(mM) |  |  |  |  |
| Trial 1 | 10 | 0.98 |  |  |
| 1 | 10 | 0.03 | 0.000003 | 3/98 |
| 2 | 10 | 0.06 | 0.000006 | 3/49 |
| 3 | 10 | 0.12 | 0.000012 | 1/8 |
| 4 | 5 | 0.24 | 0.000048 | 1/4 |
| 5 | 0.08 | 0.49 | 0.006125 | 1/2 |
| 6 | 0.08 | 0.98 | 0.01225 |  |
| 7 | 0.08 | 1.95 | 0.024375 |  |
| 8 | 0.08 | 3.9 | 0.04875 |  |
| Ammonium sulfate(mM) |  |  |  |  |
| Trial | 93.8 | 0.98 |  |  |
| 1 | 187.5 | 0.03 | 0.00000016 | 3/98 |
| 2 | 187.5 | 0.06 | 0.00000032 | 3/49 |
| 3 | 187.5 | 0.12 | 0.00000064 | 1/8 |
| 4 | 187.5 | 0.24 | 0.00000128 | 1/4 |
| 5 | 46.9 | 0.49 | 1.04478E−05 | 1/2 |
| 6 | 2.9 | 0.98 | 0.000337931 | 1 |

TABLE 2-continued

*Bacillus subtilis* ATCC 15841
MIC at 24 hours in Light

|   | PHL B(uM) | Molar ratio | Reduced PhlB |
|---|---|---|---|
| 7 | 2.9 | 1.95 | 0.000672414 |
| 8 | 2.9 | 3.9 | 0.001344828 |

TABLE 3

*Ralstonia insidiosa* ATCC 49129
MIC at 24 hours in Light

|   | PHL B(uM) | Molar ratio | Reduced PhlB |   |
|---|---|---|---|---|
| Fluorescein(uM) | | | | |
| Trial | 7.8 | 0.49 | | |
| 1 | 3.9 | 0.03 | 0.007692308 | 1/16 |
| 2 | 3.9 | 0.06 | 0.015384615 | 1/8 |
| 3 | 3.9 | 0.12 | 0.030769231 | 1/4 |
| 4 | 3.9 | 0.24 | 0.061538462 | 1/2 |
| 5 | 0.98 | 0.49 | 0.5 | |
| 6 | 0.49 | 0.98 | 2 | |
| 7 | 0.49 | 1.95 | 3.979591837 | |
| 8 | 0.49 | 3.9 | 7.959183673 | |
| NaTetraBorate(mM) | | | | |
| Trial | 10 | 0.24 | | |
| 1 | 10 | 0.03 | 0.000003 | 1/8 |
| 2 | 10 | 0.06 | 0.000006 | 1/4 |
| 3 | 10 | 0.12 | 0.000012 | 1/2 |
| 4 | 10 | 0.24 | 0.000024 | |
| 5 | 0.08 | 0.49 | 0.006125 | |
| 6 | 0.08 | 0.98 | 0.01225 | |
| 7 | 0.08 | 1.95 | 0.024375 | |
| 8 | 0.08 | 3.9 | 0.04875 | |
| Ammonium sulfate(mM) | | | | |
| Trial | 750 | 0.49 | | |
| 1 | 750 | 0.03 | 0.00000004 | 3/49 |
| 2 | 750 | 0.06 | 0.00000008 | 1/8 |
| 3 | 750 | 0.12 | 0.00000016 | 1/4 |
| 4 | 750 | 0.24 | 0.00000032 | 1/2 |
| 5 | 5.9 | 0.49 | 8.30508E−05 | 1 |
| 6 | 5.9 | 0.98 | 0.000166102 | |
| 7 | 5.9 | 1.95 | 0.000330508 | |
| 8 | 5.9 | 3.9 | 0.000661017 | |

TABLE 4

*Stenotrophomonos maltophilia* ATCC 13637
MIC at 24 hours in Light

|   | PHL B(uM) | Molar ratio | Reduced PhlB |   |
|---|---|---|---|---|
| Fluorescein(uM) | | | | |
| Trial | 7.8 | 0.49 | | |
| 1 | 1.95 | 0.03 | 0.0153846 | 1/16 |
| 2 | 1.95 | 0.06 | 0.0307692 | 1/8 |
| 3 | 3.9 | 0.12 | 0.0307692 | 1/4 |
| 4 | 0.98 | 0.24 | 0.244898 | 1/2 |
| 5 | 0.49 | 0.49 | 1 | |
| 6 | 0.49 | 0.98 | 2 | |
| 7 | 0.49 | 1.95 | 3.9795918 | |
| 8 | 0.49 | 3.9 | 7.9591837 | |
| NaTetraBorate(mM) | | | | |
| Trial | 5 | 0.24 | | |
| 1 | 2.5 | 0.03 | 0.000012 | 1/8 |
| 2 | 2.5 | 0.06 | 0.000024 | 1/4 |

TABLE 4-continued

*Stenotrophomonos maltophilia* ATCC 13637
MIC at 24 hours in Light

|   | PHL B(uM) | Molar ratio | Reduced PhlB |   |
|---|---|---|---|---|
| 3 | 2.5 | 0.12 | 0.000048 | 1/2 |
| 4 | 0.08 | 0.24 | 0.003 | |
| 5 | 0.08 | 0.49 | 0.006125 | |
| 6 | 0.08 | 0.98 | 0.01225 | |
| 7 | 0.08 | 1.95 | 0.024375 | |
| 8 | 0.08 | 3.9 | 0.04875 | |
| Ammonium sulfate(mM) | | | | |
| Trial | 375 | 0.24 | | |
| 1 | 187.5 | 0.03 | 1.6E−07 | 1/8 |
| 2 | 187.5 | 0.06 | 3.2E−07 | 1/4 |
| 3 | 93.8 | 0.12 | 1.279E−06 | 1/2 |
| 4 | 23.4 | 0.24 | 1.026E−05 | 1 |
| 5 | 2.9 | 0.49 | 0.000169 | |
| 6 | 2.9 | 0.98 | 0.0003379 | |
| 7 | 2.9 | 1.95 | 0.0006724 | |
| 8 | 2.9 | 3.9 | 0.0013448 | |

TABLE 5

*Rhizobium radiobacter* ATCC 70069
MIC at 24 hours in Light

|   | PHL B(uM) | Molar ratio | Reduced PhlB |   |
|---|---|---|---|---|
| Fluorescein(uM) | | | | |
| Trial | 0.98 | 0.24 | | |
| 1 | 0.49 | 0.03 | 0.0612245 | 1/8 |
| 2 | 0.49 | 0.06 | 0.122449 | 1/4 |
| 3 | 0.49 | 0.12 | 0.244898 | 1/2 |
| 4 | 0.49 | 0.24 | 0.4897959 | |
| 5 | 0.49 | 0.49 | 1 | |
| 6 | 0.49 | 0.98 | 2 | |
| 7 | 0.49 | 1.95 | 3.9795918 | |
| 8 | 0.49 | 3.9 | 7.9591837 | |
| NaTetraBorate(mM) | | | | |
| Trial | 2.5 | 0.12 | | |
| 1 | 0.63 | 0.03 | 4.762E−05 | 1/4 |
| 2 | 0.16 | 0.06 | 0.000375 | 1/2 |
| 3 | 0.08 | 0.12 | 0.0015 | |
| 4 | 0.08 | 0.24 | 0.003 | |
| 5 | 0.08 | 0.49 | 0.006125 | |
| 6 | 0.08 | 0.98 | 0.01225 | |
| 7 | 0.08 | 1.95 | 0.024375 | |
| 8 | 0.08 | 3.9 | 0.04875 | |
| Ammonium sulfate(mM) | | | | |
| Trial | 93.8 | 0.12 | | |
| 1 | 46.9 | 0.03 | 6.397E−07 | 1/4 |
| 2 | 46.9 | 0.06 | 1.279E−06 | 1/2 |
| 3 | 23.4 | 0.12 | 5.128E−06 | 1 |
| 4 | 2.9 | 0.24 | 8.276E−05 | |
| 5 | 2.9 | 0.49 | 0.000169 | |
| 6 | 2.9 | 0.98 | 0.0003379 | |
| 7 | 2.9 | 1.95 | 0.0006724 | |
| 8 | 2.9 | 3.9 | 0.0013448 | |

As shown in Tables 2-5, there is a synergy present according the compositions of the present invention that allows for a reduced amount of PhlB required when paired with the synergists according to the present invention. Without seeking to be limited to a particular theory of invention, it is believed that when the compositions according to the present invention are applied allow for greater uptake, enhanced light capture-activity, as well as a differential kinetic response. The additional synergists help to enhance bacterial uptake of the active ingredients while contributing to the biochemical control of the bacteria in question. It is believed the combination of these and other factors allow for rapid control of Gram-positive and Gram-negative bacteria in comparison to conventional methods.

Example 2

Yeast: Culture *Candida* on Sabouraud Dextrose Agar (SDA) at 35±1° C. for 24-48 hours until colonies are approximately 2-3 mm in diameter. Suspend ~5 colonies in 5 mL of sterile 0.8-0.9% saline solution. Vortex for 15 seconds. Adjust the cell density to that of a 0.5 McFarland Equivalence Turbidity Standard. Prepare adjusted inoculum: Dilute the cell suspension 1:2000 in RPMI 1640. Inoculate microplates by adding 100 μL to each applicable well.

Mold: Culture *Curvularia* and *Aspergillus* on SDA at 35±1° C. for 7 days or until good sporulation is obtained. Culture *Alternaria* at 30±1° C. for 7 days or until good sporulation is obtained. Harvest sporulating colonies with 0.8-0.9% saline solution and transfer to a fresh tube. Allow heavy particles to settle for 5 minutes and transfer the upper homogeneous suspension to a sterile tube and mix via vortex for 15 seconds. Read and adjust the optical density to OD (530 nm):
  *Alternaria*: 0.25-0.30
  *Aspergillus*: 0.09-0.13
  *Curvularia*: 0.25-0.30

During the *Candida* adjusted inoculum preparation, saline cell suspensions with optical densities equal to that of a 0.5 McFarland Equivalence Turbidity Standard were diluted 1:1000 in RPMI 1640, rather than 1:2000 as instructed in CLSI M27-A3. *Alternaria* was cultured at 30±1° C. for 7 days or until good sporulation was obtained.

Data Analysis/Reporting: Read microplates for visible growth (turbidity). Use the minimum inhibitory concentration (MIC).

Results are shown in Tables 6-9 below. Reduced PhlB as shown in the tables indicates the fraction by with a traditional dosage of PhlB is reduced through the synergy exhibited by the addition of the described components of the invention.

TABLE 6

*Aspergillus niger* ATCC 6275
MIC at 24 hours in Light

|  | PHL B(uM) | Molar ratio | Reduced PhlB |
|---|---|---|---|
| Fluorescein(uM) | | | |
| Trial | 1.86 | 1.93 | |
| 1 | 1.86 | 0.00 | 0.00 |
| 2 | 1.86 | 0.96 | 0.52 | ½ |
| 3 | 1.86 | 1.93 | 1.04 |
| 4 | 1.06 | 3.62 | 3.40 |
| 5 | 1.06 | 8.44 | 7.94 |
| 6 | 0.53 | 15.67 | 29.48 |
| 7 | 0.53 | 31.34 | 58.96 |
| 8 | 0.27 | 62.68 | 235.84 |
| NaTetraBorate(uM) | | | |
| Trial | 2673 | 1.93 | |
| 1 | 4999.50 | 0.00 | 0.00 |
| 2 | 313.09 | 0.96 | 0.00 | ½ |
| 3 | 313.09 | 1.93 | 0.01 |
| 4 | 154.06 | 3.62 | 0.02 |
| 5 | 154.06 | 8.44 | 0.05 |
| 6 | 79.51 | 15.67 | 0.20 |

TABLE 6-continued

*Aspergillus niger* ATCC 6275
MIC at 24 hours in Light

|  | PHL B(uM) | Molar ratio | Reduced PhlB |
|---|---|---|---|
| 7 | 79.51 | 31.34 | 0.39 |
| 8 | 79.51 | 62.68 | 0.79 |
| Ammonium sulfate(uM) | | | |
| Trial | 93749 | 3.62 | |
| 1 | 93749.05 | 0.00 | 0.0000 |
| 2 | 46875.28 | 0.96 | 0.00002 | ¼ |
| 3 | 46875.28 | 1.93 | 0.0000 | ½ |
| 4 | 23437.26 | 3.62 | 0.0002 |
| 5 | 11718.63 | 8.44 | 0.0007 |
| 6 | 5857.42 | 15.67 | 0.0027 |
| 7 | 5857.42 | 31.34 | 0.0054 |
| 8 | 5857.42 | 62.68 | 0.0107 |

TABLE 7

*Alternaria alternata* ATCC 66981
MIC at 24 hours in Light

|  | PHL B(uM) | Molar ratio | Reduced PhlB |
|---|---|---|---|
| Fluorescein(uM) | | | |
| Trial | 15.68 | 1.93 | |
| 1 | 15.68 | 0.00 | 0.00 |
| 2 | 15.68 | 0.96 | 0.06 | ¼ |
| 3 | 7.71 | 1.93 | 0.25 |
| 4 | 7.71 | 3.62 | 0.47 |
| 5 | 7.71 | 8.44 | 1.09 |
| 6 | 3.99 | 15.67 | 3.93 |
| 7 | 1.86 | 31.34 | 16.85 |
| 8 | 1.86 | 62.68 | 33.69 |
| NaTetraBorate(mM) | | | |
| Trial | 625.16 | 1.93 | |
| 1 | 625.19 | 0.00 | 0.00000 |
| 2 | 312.59 | 0.96 | 0.00010 | ½ |
| 3 | 312.59 | 1.93 | 0.00617 |
| 4 | 156.05 | 3.62 | 0.02317 |
| 5 | 78.02 | 8.44 | 0.05407 |
| 6 | 78.02 | 15.67 | 0.20083 |
| 7 | 78.02 | 31.34 | 0.20083 |
| 8 | 78.02 | 62.68 | 0.10026 |
| Ammonium sulfate(uM) | | | |
| Trial | 46874 | 3.62 | |
| 1 | 93749.05 | 0.00 | 0.0000 |
| 2 | 46875.28 | 0.96 | 0.00002 | ¼ |
| 3 | 46875.28 | 1.93 | 0.00004 | ½ |
| 4 | 23437.26 | 3.62 | 0.0002 |
| 5 | 11718.63 | 8.44 | 0.0007 |
| 6 | 5857.42 | 15.67 | 0.0027 |
| 7 | 5857.42 | 31.34 | 0.0054 |
| 8 | 5857.42 | 62.68 | 0.0107 |

TABLE 8

*Curvularia lunata* ATCC 12017
MIC at 24 hours in Light

|  | PHL B(uM) | Molar ratio | Reduced PhlB |
|---|---|---|---|
| Fluorescein(uM) | | | |
| Trial | 15.68 | 3.62 | |
| 1 | 15.68 | 0.00 | 0.00 |
| 2 | 31.89 | 0.96 | 0.03 | ¼ |
| 3 | 15.68 | 1.93 | 0.12 | ½ |

TABLE 8-continued

*Curvularia lunata* ATCC 12017
MIC at 24 hours in Light

|   | PHL B(uM) | Molar ratio | Reduced PhlB |
|---|---|---|---|
| 4 | 3.99 | 3.62 | 0.91 |
| 5 | 3.99 | 8.44 | 2.12 |
| 6 | 3.99 | 15.67 | 3.93 |
| 7 | 1.06 | 31.34 | 29.48 |
| NaTetraBorate(uM) | | | |
| Trial | 4999.50 | 7.835 | |
| 1 | 312.59 | 0.48 | 0.0062 | ¼ |
| 2 | 312.59 | 0.96 | 0.025 | ½ |
| 3 | 156.05 | 1.93 | 0.1017 | |
| 4 | 78.02 | 3.62 | 0.0062 | |
| 5 | 78.02 | 8.44 | 0.0031 | |
| 6 | 78.02 | 15.67 | 0.0015 | |
| 7 | 78.02 | 31.34 | 0.0008 | |
| 8 | 78.02 | 62.68 | 0.0004 | |
| Ammonium sulfate(mM) | | | |
| Trial | 750000 | 8.44 | |
| 1 | 46874.53 | 0.96 | 0.0000206 | ⅛ |
| 2 | 46874.53 | 1.93 | 0.0000411 | ¼ |
| 3 | 23437.26 | 3.62 | 0.0001543 | ½ |
| 4 | 23437.26 | 8.44 | 0.0001543 | |
| 5 | 11722.42 | 15.67 | 0.0000206 | |
| 6 | 5857.42 | 31.34 | 0.0000103 | |
| 7 | 5857.42 | 62.68 | 0.0000051 | |
| 8 | 5857.42 | 125.36 | 0.0000026 | |

TABLE 9

*Candida albicans* ATCC 10231
MIC at 24 hours in Light

|   | PHL B(uM) | Molar ratio | Reduced PhlB |   |
|---|---|---|---|---|
| Fluorescein(uM) | | | | |
| Trial | 2001.22 | 62.68 | | |
| 1 | 2001.22 | 0.00 | 0.0000 | |
| 2 | 499.64 | 0.96 | 0.0019 | 1/64 |
| 3 | 499.64 | 1.93 | 0.0039 | 1/32 |
| 4 | 499.64 | 3.62 | 0.0072 | 1/16 |
| 5 | 499.64 | 8.44 | 0.0169 | ⅛ |
| 6 | 499.64 | 15.67 | 0.0314 | ¼ |
| 7 | 499.64 | 31.34 | 0.0627 | ½ |
| 8 | 124.91 | 62.68 | 0.5018 | |
| NaTetraBorate(uM) | | | | |
| Trial | 9999 | 125 | | |
| 1 | 9999 | 0.96 | 0.00010 | 1/128 |
| 2 | 312.59 | 1.93 | 0.00617 | 1/64 |
| 3 | 156.05 | 3.62 | 0.02317 | 1/32 |
| 4 | 156.05 | 8.44 | 0.05407 | 1/16 |
| 5 | 78.02 | 15.67 | 0.20083 | ⅛ |
| 6 | 156.05 | 31.34 | 0.20083 | ¼ |
| 7 | 625.19 | 62.68 | 0.10026 | |
| 8 | 625.19 | 125.36 | 0.20051 | ½ |
| Ammonium sulfate(uM) | | | | |
| Trial | 750000 | 125.36 | | |
| 1 | 750000.00 | 0.00 | 0.0000 | |
| 2 | 187498.11 | 0.96 | 0.00001 | 1/125 |
| 3 | 93749.05 | 1.93 | 0.00002 | 1/64 |
| 4 | 23437.26 | 3.98 | 0.0002 | 1/32 |
| 5 | 23437.26 | 7.83 | 0.0003 | 1/16 |
| 6 | 23437.26 | 15.67 | 0.0007 | ⅛ |
| 7 | 23437.26 | 31.34 | 0.0013 | ¼ |
| 8 | 11714.85 | 62.68 | 0.0054 | ½ |

As shown in Tables 6-9, there is a synergy present according the compositions of the present invention that allows for a reduced amount of PhlB required when paired with the synergists according to the present invention. Without seeking to be limited to a particular theory of invention, it is believed that when the compositions according to the present invention are applied allow for greater uptake, enhanced light capture-activity, as well as a differential kinetic response. The additional synergists help to enhance bacterial uptake of the active ingredients while contributing to the biochemical control of the bacteria in question. It is believed the combination of these and other factors allow for rapid control of fungi in comparison to conventional methods.

The inventions being thus described, it will be obvious that the same may be varied in many ways. Such variations are not to be regarded as a departure from the spirit and scope of the inventions and all such modifications are intended to be included within the scope of the following claims.

The above specification provides a description of the manufacture and use of the disclosed compositions and methods. Since many embodiments can be made without departing from the spirit and scope of the invention, the invention resides in the claims.

What is claimed is:

1. An antimicrobial composition comprising:
   from about 0.01 wt. % to about 50 wt. % of a xanthene dye, wherein the xanthene dye is phloxine B; and
   one or more of a synergistic component comprising from about 0.01 wt. % to about 60 wt. % of fluorescein, from about 50 wt. % to about 95 wt. % of sodium tetraborate, or from about 50 wt. % to about 100 wt. % of ammonium sulfate, wherein the synergistic component acts in synergy with the xanthene dye,
   wherein the xanthene dye and the synergistic component are present in a ratio from about 0.001:1 to about 1:0.001.

2. The composition according to claim 1, wherein the xanthene dye is present in an amount of about 0.1 wt. % to about 10 wt. %.

3. The composition of claim 1, wherein the synergistic component is fluorescein.

4. The composition of claim 3, wherein the fluorescein is present in an amount of at least 50 micromoles.

5. The composition of claim 3, wherein the fluorescein is present in an amount of from about 0.05 wt. % to about 35 wt. %.

6. The composition of claim 1, wherein the synergistic component is sodium tetraborate.

7. The composition of claim 6, wherein the sodium tetraborate is present in an amount of at least 2 millimoles.

8. The composition of claim 6, wherein the sodium tetraborate is present in an amount of about 70 wt. % to about 95 wt. %.

9. The composition of claim 1, wherein the synergistic component is ammonium sulfate.

10. The composition of claim 9, wherein the ammonium sulfate is present in an amount of at least 75 millimoles.

11. The composition of claim 9, wherein the ammonium sulfate is present in an amount of from about 70 wt. % to about 100 wt. %.

12. The composition according to claim 1, further comprising at least one additional functional ingredient.

13. The composition according to claim 12, wherein the at least one additional functional ingredient is selected from the group of: antimicrobial compounds, surfactants, extenders, solvents, spontaneity promoters, carriers, emulsifiers, dispersants, frost protectants, sun protectant, thickeners and adjuvants, and insect food sources.

14. The composition according to claim 12, wherein the at least one additional functional ingredient is present in an amount of from about 0.01% to about 95% by weight of active compound.

* * * * *